United States Patent [19]

Maurer et al.

[11] Patent Number: 4,940,698

[45] Date of Patent: Jul. 10, 1990

[54] INSECTICIDAL THIONOPHOSPHONATES

[75] Inventors: Fritz Maurer, Wuppertal; Bernhard Homeyer, Leverkusen; Wolfgang Behrenz, Overath, all of Fed. Rep. of Germany

[73] Assignee: Bayer Aktiengesellschaft, Leverkusen, Fed. Rep. of Germany

[21] Appl. No.: 237,241

[22] Filed: Aug. 26, 1988

[30] Foreign Application Priority Data

Sep. 2, 1987 [DE] Fed. Rep. of Germany ....... 3729263

[51] Int. Cl.$^5$ .......................... A01N 57/24; C07F 9/65
[52] U.S. Cl. ....................................... 514/86; 544/243
[58] Field of Search ........................... 544/243; 514/86

[56] References Cited

U.S. PATENT DOCUMENTS 2,754,243  7/1956  Gysin et al. ............................ 514/86
3,216,894  11/1965  Lorenz et al. .................. 544/243 X
4,155,999  5/1979  Maurer et al. ......................... 514/86

FOREIGN PATENT DOCUMENTS 1140580  12/1962  Fed. Rep. of Germany .
3445465   6/1986  Fed. Rep. of Germany ........ 514/86

Primary Examiner—Diana G. Rivers
Attorney, Agent, or Firm—Sprung Horn Kramer & Woods

[57] ABSTRACT

Insecticidal O-(6-methyl-2-alkyl-pyrimidin-4-yl) O-alkyl thionoalkanephosphonates of the formula

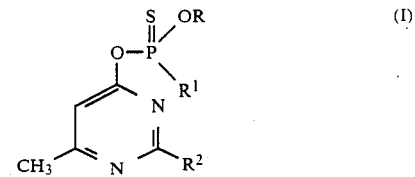

in which
R stands for methyl or ethyl,
R$^1$ stands for methyl or ethyl and
R$^2$ stands for isopropyl or tert-butyl.

13 Claims, No Drawings

INSECTICIDAL THIONOPHOSPHONATES

The present invention relates to new O-(6-methyl-2-alkyl-pyrimidin-4-yl)O-alkyl thionoalkanephosphonates, a process for their preparation and their use as pest-combating agents, preferably as insecticides.

It has already been disclosed that certain O-(2,6-dialkyl-pyrimidin-4-yl) O-alkyl thionoalkanephosphonates, such as, for example, O-(2-methyl-6-tert.-butyl-pyrimidin-4-yl) O-ethyl thionomethanephosphonate and O-(2,6-di-methyl-pyrimidin-4-yl) O-methyl thionoethanephosphonate are suitable for combating insects (compare DE-OS (German Published Specification) No. 1,140,580 and DE-OS (German Published Specification) No. 2,639,433). However, the insecticidal action of these known compounds is not always satisfactory, in particular at low application rates or active compound concentrations and with respect to the duration of action.

New O-(6-methyl-2-alkyl-pyrimidin-4-yl) O-alkyl thionoalkanephosphonates of the general formula (I)

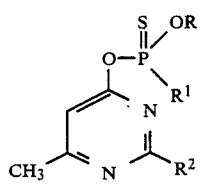

in which
R stands for methyl or ethyl,
R¹ stands for methyl or ethyl and
R² stands for isopropyl or tert-butyl, have now been found.

It has further been found that the new O-(6-methyl-2-alkyl-pyrimidin-4-yl) O-alkyl thionoalkanephosphonates of the formula (I) are obtained when 6-methyl-2-alkyl-4-hydroxy-pyrimidines of the general formula (II)

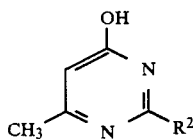

in which
R² has the abovementioned meaning, or their alkali metal salts, alkaline earth metal salts or ammonium salts are reacted with O-alkyl chlorothionoalkanephosphonates of the formula (III)

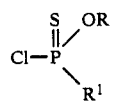

in which
R and R¹ have the abovementioned meaning, if appropriate in the presence of an acid-acceptor and if appropriate in the presence of a diluent.

Finally, it has been found that the new O-(6-methyl2-alkyl-pyrimidin-4-yl) O-alkyl thionoalkanephosphonates of the formula (I) are distinguished by very strong arthropodicidal, in particular insecticidal activity.

The new compounds of the formula (I) show, in particular, an outstanding action against Orthoptera, such as, for example, *Blattella germanica* and Coleoptera, such as, for example, *Sitophilus granarius*. The active compounds according to the invention also show outstanding action against soil insects (that is insects which occur in or on the soil or in the vicinity of the soil), such as, for example, *Phorbia antiqua* grubs and *Diabrotica balteata* larvae.

Surprisingly, the O-(6-methyl-2-alkyl-pyrimidin-4-yl) O-alkyl thionoalkanephosphonates of the formula (I) show considerably stronger insecticidal action than the abovementioned O-(2,6-dialkyl-pyrimidin-4-yl) O-alkyl thionoalkanephosphonates. The substances according to the invention thus represent a valuable enrichment of the art.

Particularly important compounds of the formula (I) which may be mentioned are: O-(6-methyl-2-tert-butyl-pyrimidin-4-yl) O-methyl thionoethanephosphonate and O-(6-methyl-2-isopropyl-pyrimidin-4-yl) O-methyl thionoethanephosphonate.

If, for example, 6-methyl-2-tert-butyl-4-hydroxypyrimidine and O-methyl chlorothionoethanephosphonate are used as starting materials, then the course of the reaction can be represented by the following equation:

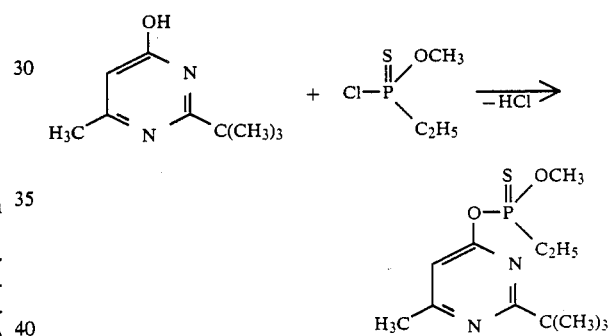

Formula (II) provides a definition of the 6-methyl-2-alkyl-4-hydroxy-pyrimidines to be used as starting materials. Those alkali metal salts or alkaline earth metal salts (which are preferred in the process according to the invention) preferably employed are the sodium salts, potassium salts or calcium salts.

Examples which may be mentioned are 6-methyl-2-tert-butyl-4-hydroxy-pyrimidine and 6-methyl-2-isopropyl-4-hydroxy-pyrimidine.

The 6-methyl-2-alkyl-4-hydroxy-pyrimidines of the formula (II) are known (compare DE-OS (German Published Specification) No. 2,065,698 or J. Chem. Soc. (London) 1963, page 5652).

The O-alkyl chlorothionoethanephosphonate of the formula (III) further to be used as starting materials are already known (compare DE-OS (German Published Specification) No. 1,078,124, British Patent Specification No. 1,450,284 and DE-OS (German Published Specification) No. 2,920,172).

The process according to the invention for the preparation of the new compounds of the formula (I) is preferably carried out using diluents and acid-acceptors.

In this case, suitable diluents are practically all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylene sulphone and hexamethylphosphoric triamide.

Acid-acceptors which can be employed in the process according to the invention are all acid-binding agents which are conventionally utilizable for reactions of this type. Preferably suitable are alkali metal hydroxides such as, for example, sodium hydroxide and potassium hydroxide, alkaline earth metal hydroxides such as, for example, calcium hydroxide, alkali metal carbonates and alkali metal alcoholates such as sodium carbonate and potassium carbonate, sodium tert-butylate and potassium tert-butylate, and furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

The reaction temperatures can be varied within a substantial range when carrying out the process according to the invention. In general, the reaction is carried out at temperatures between 0° C. and 100° C., preferably at temperatures between 10° C. and 80° C.

The process according to the invention is generally carried out under atmospheric pressure. However, it is also possible to work at elevated or reduced pressure.

For carrying out the process according to the invention, the starting materials of the formulae (II) and (III) are generally employed in approximately equimolar amounts. However, an excess of up to 10% of one component or the other is possible without problems.

The reaction components are generally combined in one of the abovementioned solvents and stirred for several hours, by means of which the temperature is kept in the abovementioned range.

For working up, which takes place by customary methods, the mixture is concentrated, the residue is taken up in a solvent which is practically immiscible with water, such as, for example, toluene, and the solution is washed using water and dried using a customary drying agent, such as, for example, sodium sulphate. After filtration, the solvent is removed from the filtrate by distillation in the water jet vacuum.

The new compounds are produced in the form of oils which cannot be distilled without partial decomposition, but are freed from the last volatile constituents by so-called "incipient distillation", that is by relatively long heating under reduced pressure to moderately raised temperatures, and are purified in this manner. The refractive index is used for their characterization.

The active compounds are suitable for combating animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oryzaephilus surinamensis,* Antho nomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The active compounds according to the invention are distinguished by an outstanding insecticidal activity, in particular in combating Orthoptera species, such as, for example, *Blattella germanica* and *Coleoptera* species, such as, for example, *Sitophilus granarius.*

On account of their high stability, the active compounds according to the invention can also be well employed for combating soil insects, such as, for example, *Phorbia antiqua* grubs and *Diabrotica balteata* larvae.

Some of the active compounds according to the invention also show leaf insecticidal action.

In particular, the following compounds of the formula (I) according to the invention are particularly preferred: O-(6-methyl-2-tert-butyl-pyrimidin-4-yl) O-methyl thionoethanephosphonate and O-(6-methyl-2-isopropylpyrimidin-4-yl) O-methyl thionoethanephosphonate.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The preparation and the use of the compounds according to the invention is illustrated by the following examples.

PREPARATION EXAMPLES

Example 1

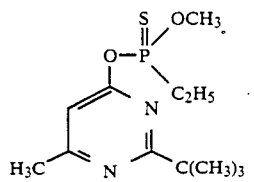

15.85 g (0.1 mol) of O-methyl chlorothionoethanephosphonate are added at 20° C. with stirring to a mixture of 16.6 g (0.1 mol) of 6-methyl-2-tert-butyl-4-hydroxy-pyrimidine, 20.7 g (0.15 mol) of potassium carbonate and 200 ml of acetonitrile and the mixture is stirred for 15 hours at 20° C. After concentration, the residue is taken up in 100 ml of toluene, and the solution is washed twice using 100 ml of water each time, dried using sodium sulphate and filtered. The solvent is removed from the filtrate by distillation under reduced pressure at about 50° C.

26.2 g (91% of theory) of O-(6-methyl-2-tert-butyl-pyrimidin-4-yl) O-methyl thionoethanephosphonate are obtained as an oily residue of refractive index $n_D^{21} = 1.5172$.

The compounds of the formula (I) shown in the table below can be prepared analogously to Example 1 and corresponding to the general description of the preparation process according to the invention.

TABLE

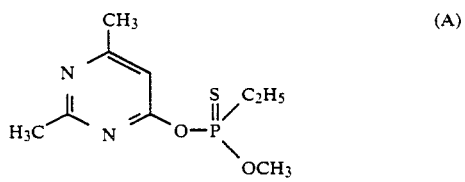

| Example No. | R | $R^1$ | $R^2$ | Refractive index |
|---|---|---|---|---|
| 2 | $CH_3$ | $C_2H_5$ | $C_3H_7$-i | $n_D^{22} = 1.5205$ |
| 3 | $CH_3$ | $CH_3$ | $C_4H_9$-t | |
| 4 | $C_2H_5$ | $C_2H_5$ | $C_4H_9$-t | |
| 5 | $C_2H_5$ | $CH_3$ | $C_4H_9$-t | |

USE EXAMPLES

The compounds given below were employed as comparison compounds in the following use examples:

(A)

H₃C pyrimidine structure with S/OP(OCH₃)(C₂H₅)

(DE-OS (German Published Specification) No. 1,140,580, Example 11)

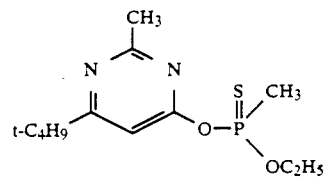

(DE-OS (German Published Specification) No. 2,639,433, Example 3).

EXAMPLE A

Test insects: *Blatella germanica*
Number of test insects: 25
Solvent: acetone 2 parts by weight of active compound are taken up in 1,000 parts by volume of solvent. The solution thus obtained is diluted with further solvent to the desired concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per m² of filter paper varies, depending on the concentration of the active compound solution. The stated number of test insects is then introduced into the Petri dish, and the dish is covered with a glass lid.

The condition of the test insects is checked 3 days after setting up the tests. The destruction in % is determined. 100% means that all test insects been killed; 0% means that no test insects have been killed.

In this test, the compounds of Examples (1) and (2) showed a degree of destruction of 100% at a concentration of 0.002%, for example, whereas the comparison substances (A) and (B) showed no destruction (0%) at the same concentration.

EXAMPLE B

Test insects: *Sitophilus granarius*
Number of test insects: 25
Solvent: acetone 2 parts by weight of active compound are taken up in 1,000 parts by volume of solvent. The solution thus obtained is diluted with further solvent to the desired concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per m² of filter paper varies, depending on the concentration of the active compound solution. The stated number of test insects is then introduced into the Petri dish, and the dish is covered with a glass lid.

The condition of the test insects is checked 3 days after setting up the tests. The destruction in % is determined. 100% means that all test insects have been killed; 0% means that no test insects have been killed.

In this test, the compounds of Examples (1) and (2) showed a degree of destruction of 100% at a concentration of 0.002%, for example, whereas the comparison substances (A) and (B) showed no destruction (0%) at the same concentration.

EXAMPLE C

Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the compounds of Examples (1) and (2) showed a degree of destruction of 100% at a concentration of 5 ppm, for example, whereas the comparison compound (A) showed no destruction (0%) at the same concentration.

EXAMPLE D

Test insect: *Diabrotica balteata*-larvae in the soil
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration. The preparation of active compound is intimately mixed with soil. The concentration of the active compound in the preparation is of practically no importance here, only the amount by weight of active compound per unit volume of soil, which is given in ppm (=mg/l), being decisive. The soil is filled into 0.5 l pots and the pots are left to stand at 20° C. Immediately after the start, 6 pregerminated corn grains are planted in each pot. After 2 days, the corresponding test insects are introduced into the treated soil. After a further 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the compounds of Examples (1) and (2) showed a degree of destruction of 100% at a concentration of 5 ppm, for example, whereas the comparison compound (A) showed no destruction (0%) at the same concentration.

It will be appreciated that the instant specification and claims are set forth by way of illustration and not limitation, and that various modifications and changes may be made without departing from the spirit and scope of the present invention.

What is claimed is:

1. An O-(6-methyl-2-alkyl-pyrimidin-4-yl) O-alkyl thionoalkanephosphonate of the formula

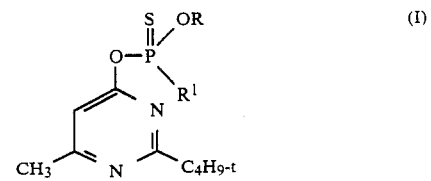

in which
R stands for methyl or ethyl, and
$R^1$ stands for methyl or ethyl.

2. A compound according to claim 1, wherein such compound is O-(6-methyl-2-t-butyl-pyrimidin-4-yl) O-methyl thionoethanephosphonate of the formula

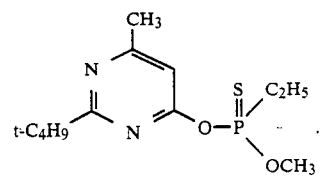

3. A compound according to claim 1, wherein such compound is O-(6-methyl-2-t-butyl-pyrimidin-4-yl) O-methyl thionoethanephosphonate of the formula

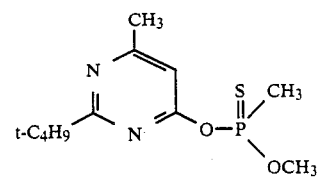

4. A compound according to claim 1, wherein such compound is O-(6-methyl-2-t-butyl-pyrimidin-4-yl) O-ethyl thionoethanephosphonate of the formula

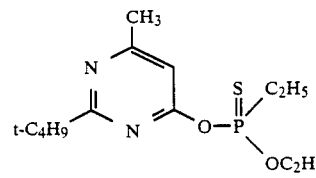

5. A compound according to claim 1, wherein such compound is O-(6-methyl 2-t-butyl-pyrimidin-4-yl) O-ethyl thionoethanephosphonate of the formula

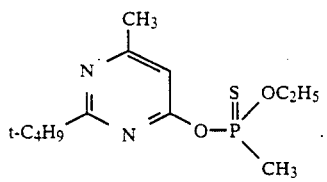

6. An insecticidal composition comprising an insecticidally effective amount of a compound according to claim 1 and a diluent.

7. A method of combating insects which comprises applying to such insects or to an insect habitat an insecticidally effective amount of a compound according to claim 1.

8. The method according to claim 7, wherein such compound is

O-(6-methyl-2-t-butyl-pyrimidin-4-yl) O-methyl thionoethanephosphonate,

O-(6-methyl-2-t-butyl-pyrimidin-4-yl) O-methyl thionoethanephosphonate,

O-(6-methyl-2-t-butyl pyrimidin-4-yl) O-ethyl thionoethanephosphonate,

O-(6-methyl-2-t-butyl-pyrimidin-4-yl) O-ethyl thionoethanephosphonate.

9. An O-(6-methyl-2-alkyl-pyrimidin-4-yl) O-alkyl thionoalkanephosphona of the formula

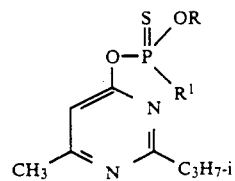

in which,
one of R and R¹ stands for methyl and the other stands for ethyl.

10. A compound according to claim 9, wherein such compound is O-(6-methyl-2-isopropyl-pyrimidin-4-yl) O-methyl thionoethanephosphonate of the formula

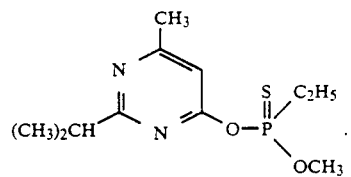

11. An insecticidal composition comprising an insecticidally effective amount of a compound according to claim 9, and a diluent.

12. A method of combating insects which comprises applying to such insects or to an insect habitat an insecticidally effective amount of a compound according to claim 9.

13. A method of combating insects which comprises applying to such insects or to an insect habitat an insecticidally effective amount of a compound according to claim 10.

* * * * *

UNITED STATES PATENT AND TRADEMARK OFFICE
CERTIFICATE OF CORRECTION

PATENT NO. : 4,940,698

DATED : July 10, 1990

INVENTOR(S) : Maurer et al.

It is certified that error appears in the above-identified patent and that said Letters Patent is hereby corrected as shown below:

Col. 10, claim 3 line 44  Delete " thionoethanephosphonate " and substitute -- thionomethanephosphonate --

Col. 10, claim 5 line 68  Delete " thionoethanephosphonate " and substitute -- thionomethanephosphonate --

Col. 11, claim 8 line 27  Delete " thionoethanephosphonate " and substitute -- thionomethanephosphonate --

Col. 11, claim 8 line 33  Delete " thionoethanephonate " and substitute -- thionomethanephosphonate --

Col. 11, claim 9 line 35  Delete " thionoalkanephosphona " and substitute -- thionoalkanephosphonate --

Signed and Sealed this

Fifth Day of May, 1992

Attest:

DOUGLAS B. COMER

Attesting Officer

Acting Commissioner of Patents and Trademarks